United States Patent
Schwartz et al.

(10) Patent No.: US 6,932,838 B2
(45) Date of Patent: Aug. 23, 2005

(54) VENOUS VALVULOPLASTY DEVICE AND METHOD

(75) Inventors: Robert S. Schwartz, Rochester, MN (US); Robert A. Van Tassel, Excelsior, MN (US)

(73) Assignee: TriCardia, LLC, Excelsior, MN (US)

( * ) Notice: Subject to any disclaimer, the term of this patent is extended or adjusted under 35 U.S.C. 154(b) by 226 days.

(21) Appl. No.: 09/968,301

(22) Filed: Oct. 1, 2001

(65) Prior Publication Data

US 2002/0099439 A1 Jul. 25, 2002

Related U.S. Application Data (60) Provisional application No. 60/236,501, filed on Sep. 29, 2000.

(51) Int. Cl.$^7$ .................................................. A61F 2/06
(52) U.S. Cl. ..................... 623/1.23; 623/1.36; 606/151
(58) Field of Search ............................ 623/1.22, 1.23, 623/1.24, 1.36, 66.1; 606/151, 158, 139, 142, 143; 128/898

(56) References Cited

U.S. PATENT DOCUMENTS

| | | | | |
|---|---|---|---|---|
| 5,147,389 A | * | 9/1992 | Lane ........................ | 623/1.24 |
| 5,211,649 A | * | 5/1993 | Kohler et al. ................ | 606/139 |
| 5,476,471 A | * | 12/1995 | Shifrin et al. ................ | 606/151 |
| 5,741,274 A | * | 4/1998 | Lenker et al. ............... | 606/142 |
| 5,810,851 A | | 9/1998 | Yoon | |
| 6,319,275 B1 | * | 11/2001 | Lashinski et al. ........... | 623/1.11 |
| 6,695,878 B2 | | 2/2004 | McGuckin et al. | |
| 2002/0002401 A1 | | 1/2002 | McGuckin, Jr. et al. | |

FOREIGN PATENT DOCUMENTS

| | | |
|---|---|---|
| DE | 44 12 311 A1 | 10/1995 |
| EP | 0 928 598 A2 | 7/1999 |
| WO | WO 97/40755 A1 | 11/1997 |
| WO | WO 99/62431 A1 | 12/1999 |

* cited by examiner

Primary Examiner—Corrine McDermott
Assistant Examiner—Thomas J Sweet
(74) Attorney, Agent, or Firm—Inskeep Intellectual Property Group, Inc.

(57) ABSTRACT

A device 10 and method for replacing or restoring competence to incompetent valves. The device 10 is inserted percutaneously or surgically and is preferably constructed of a material capable of promoting cellular ingrowth such that, eventually, native biologic tissue completely covers the device 10 insulating the blood flow therefrom. The material is preferably bioabsorbable over time, allowing the device to harbor the regeneration of a valve structure and to later become absorbed by the body. The device is sized and arranged to mimic the valve it is replacing or repairing.

20 Claims, 9 Drawing Sheets

VENOUS VALVULOPLASTY DEVICE AND METHOD

CROSS REFERENCE TO RELATED APPLICATION

This application claims the priority of U.S. Provisional Ser. No. 60/236,501, filed on Sep. 29, 2000.

BACKGROUND OF THE INVENTION

The venous valves found throughout the venous system assist the flow of blood through the veins and returning to the heart by preventing blood flow reversal. As a majority of venous blood flow is against gravity while a person is standing, incompetent or destroyed venous valves often result in adverse medical conditions, especially in the lower extremities. For example, deep venous hypertension may occur and give rise to clots, lymphedema, skin discoloration, varicose veins and venous ulcers.

The leading cause of venous valve incompetence is venular dilation. When a vein loses elasticity and becomes dilated, the valve cusps become too radially displaced from each other to coapt and prevent backflow. The cusps themselves, however, may not be damaged or stressed, such that restoring elasticity to the vein, or otherwise mechanically restricting the dilation, would allow the cusps to coapt and regain function.

Another type of venous valve incompetence results from damaged cusps. This condition may arise in the presence or absence of dilated veins. Damaged valves must be replaced in order to restore the function of the vein segment.

Reparation of damaged or otherwise incompetent venous valves has been largely limited to autograft procedures. Autograft procedures, though effective, are undesirable as they require the location and excision of healthy, autologous vein segments from other areas of the body. The excised segment must nearly match the size of the segment being replaced, making the location of a replacement vein a sometimes difficult task. An alternative to harvesting healthy vein segments having functional venous valves would be readily advantageous.

Developing a prosthetic or bioprosthetic valve that exhibits, if not improves upon, the functioning characteristics of healthy, natural valves is a task ripe with obstacles. For instance, the venous valves of the lower extremities are very thin. As the veins themselves are narrow, a prosthetic valve would require cusps which are also very thin, to avoid disrupting the blood flow past the valve. The prosthetic cusps, in addition to being thin, must perform to prevent blood flow reversal. Adequate performance necessarily means closing and opening as many as one hundred thousand times a day.

Additionally, the valve must be predictably accepted by the body and remain functional for many years. If the body rejects the valve, or if it malfunctions, many complications could arise, requiring a second surgery to remove the prosthetic valve and repair the vein segment using an alternative method.

SUMMARY OF THE INVENTION

The present invention pertains to the restoration of venous valve function in a vein segment. The invention includes a venous valvuloplasty method that can be performed percutaneously or surgically to restore competence to destroyed or otherwise incompetent valves.

The invention also provides a device usable to restore competence to valves that, due to dilation, contain healthy valve cusps that no longer coapt. The device acts to mechanically constrict the vein, thereby reestablishing valve competence. This device generally comprises a venuloplasty ring. The ring, when installed, contracts the size of the targeted vein near a native valve that has been rendered incompetent due to venular dilation. Included are embodiments of the ring that are constructed and arranged to be installed within the lumen of the vein, and embodiments that are constructed and arranged to be installed around the outside of the vein. These may be delivered by percutaneously using a catheter or delivery system including an expansion capability, or surgically.

One aspect of the ring is an ability to contract, thereby reducing the vein diameter and restoring competence to the native valve. Though one ring in close proximity to the venous valve may be enough to restore competence, more rings may be used in close proximity to the valve for this purpose. Preferably, at least one ring is used on either side of the native valve. Alternatively, a single device or ring assembly may be provided having integral ring elements present on either side of the native valve, joined by a connecting member. The connecting member provides structural stability and increased anchoring capabilities to the device. The ring assembly is placed within the lumen of the vein such that the cross member lies between cusps, so as not to cause interference with cusp movement. As the cross member is largely a positioning tool, it is envisioned that a bioabsorbable cross member is used which quickly dissolves once the rings of the ring assembly are firmly attached to the vein walls.

The internal embodiment of the present invention includes a mechanism for adhering to the interior walls of the vein such that the vein may be pulled inwardly to restore competence to the valve cusps. The grabbing mechanism preferably includes a plurality of projections capable of penetrating and catching the walls of the vein. The projections may include barbs, hooks, umbrella connectors, or the like. Alternatively or additionally, an adhesive could be used. Contact between the vein and the grabbing mechanism is established using a mechanical or inflatable expansion system to increase the diameter of the ring or ring assembly until the outer diameter of the device exceeds the inner diameter of the vein, thereby forcing the projections through the venous tissue. The expansion device is then retracted and removed, allowing the spring characteristics of the ring to restore the ring to the original diameter, thereby contracting the vein to a desired size as the grabbing mechanism maintains positive contact between the ring and the vein.

The external embodiment of the device may include a cuff, surgically placed around the outside wall of the vein, proximate the venous valve. Like the internal embodiment, the external device has spring qualities such that, when released, the device squeezes the vein to a desired diameter, thereby restoring competence.

The device of the present invention is constructed of a biocompatible material, such as a metal or polymer, that does not substantially affect the surrounding tissue. Preferably, the ring is fabricated from a material, such as a fabric or polymer, that is porous so that it may become infiltrated with cells and eventually becomes a living structure. Thus, once infiltrated, the device surfaces become completely biologic, preventing blood flow from contacting anything other than the newly developed, natural cells. The device may further be bioabsorbable, becoming resorbed by the body after a predetermined period, thereby leaving a cuff of biologic tissue that performs the diameter reduction function by way of the newly grown fibrous tissue.

The material of the device may be coated to enhance cellular ingrowth. This coating may comprise fibrin, fibronectin, elastin, elastin fragments, collagen, mucopolysaccharides, glycosaminoglycans, extracellular matrix, taxol, or other biomolecule useful for attracting and keeping cells and fibroblasts and/or myofibroblasts at the site. The coating may further include a drug eluting substance, such as rapamycin, actinomycin D, other macrolide antibiotics, taxol/taxanes, to prevent cell overgrowth.

Further, the material and dimensions are such that the device may be collapsible to the extent that the ring responds to natural muscle contractions. Thus, the device should not interfere with the circulatory system's natural physiologic pumping action.

One embodiment of the device provides a somewhat cylindrical ring, the wall of which having a cross section shaped to form a sinus, or slight cavity, behind the downstream side (the side toward the heart) of each of the native cusps. Similar in function to the Sinuses of Valsalva, these sinuses assist the valve in closing when pressure/flow reverses by providing a place for blood flow to act on the downstream sides of the cusps.

To further enhance the hydrodynamics of the cylindrical ring device, the cross section of the wall may further form a nozzle configuration which promotes laminar flow. It is envisioned that such cylindrical rings are placed on either side of the native valve such that the nozzle-like cross-sectional variances are present at both the inlet and outlet ends of the prosthesis. In addition to facilitating laminar blood flow, the resultant increase in velocity past the cusps, lessens the likelihood of thrombosis/thrombus formation behind the valve, which may eventually occlude the valve. As mentioned above, the porous material promotes an initial thrombus formation on the cusp material, however, once formed, the smooth, natural surface of the biologic growth, combined with the nozzle effect, will act to prevent excessive thrombus development.

A related embodiment provides a device useable as a percutaneous occluder. The occluder is placed percutaneously in a vein and contracted sufficiently such that no blood may pass through it. Alternatively, a membrane may be used to block the flow of blood, thereby requiring less contraction of the vein walls to achieve occlusion. Use of this device provides the same effect as ligating the tributaries of the saphenous vein.

Another aspect of the present invention includes an imbedded transducer. Recent advances in transducer miniaturization make it possible to attach one or more transducers to the disclosed devices. These transducers may be used to measure blood pressure, flow, temperature, thrombosis, or other physiologic variables.

The present invention also provides a device suitable for replacing valves having damaged cusps. This prosthetic venous valve is extremely thin, having cusps which are preferably less than 100 microns thick. The supporting ring for these thin cusps is preferably a fiber mesh of a material having a high tensile strength, such as a polymer or metal. The mesh may be coated with an anti-coagulant, such as heparin, to prevent valve and venous clotting. The extremely thin cusps mimic those of the valves native to the lower extremities.

The prosthetic venous valve cusps of the present invention are preferably porous, permitting them to become living structures as cellular ingrowth is facilitated by the fibers. At the same time, the material performs biologic functions, such as providing an anti-coagulant, if and when an endothelial lining develops. The porosity of the device permits fibrin and/or platelet thrombus to form within the matrix. The "healing" process will thus result in tissue growth including endothelialization of the valve surface. The pore size is preferably between 10 and 100 microns. Additionally, the pores are of an interconnected, "open pore" structure. Thus, the pores are constructed and arranged to encourage cell ingrowth and vascularization/angiogenesis, thereby further supporting the structure.

In addition to the cusps, the support structure may be partially made from the same fiber arrangement, permitting the support structure to also become a living structure once the pores fill with thrombus and "heal" with cells. The support structure may be coated with a biomolecule and/or heparin to assist in cell ingrowth and anti-thrombogenicity.

The material of the prosthetic valve may be coated to enhance cellular ingrowth. This coating may comprise fibrin, fibronectin, elastin, elastin fragments, collagen, mucopolysaccharides, glycosaminoglycans, extracellular matrix, taxol or other biomolecule useful for attracting and keeping cells and fibroblasts and/or myofibroblasts at the site. The coating may further include a drug eluting substance, such as rapamycin, to prevent cell overgrowth.

The cusps, in addition to being extremely thin, are shaped and arranged to lie flat against the vein wall or wall of the prosthetic valve support when the valve is open. Especially true in the tricuspid embodiment, the shape of the cusps is preferably characterized by having an arc length at the downstream edge of the cusp which is approximately equal to the arc length of the support structure between the two points where this edge of the cusp is attached to the support structure. This mathematical relationship is most easily envisioned by imagining a small, somewhat elongate envelope, such as that used to hold a key. Undisturbed and empty, the envelop lies flat because the length of one side of the envelop is equal to that of the other side. If the two edges are pressed towards each other, the envelop opens, each side necessarily having the same arc length. If the edges are held in this relationship and one side of the envelop is pressed toward the other, the side will eventually invert and lie flush against the other side. This mimics the action of the cusps of a tricuspid valve. More accurate representation is provided if three of these envelops are arranged in a circle, the inside edges of the envelops represent the cusps. Each of the cusps have two attachment points, adjacent attachment points from adjacent cusps being very close, approximately 120° apart. As the cusps open and close, the free edges of the cusps travel from being relatively flush with the inner walls of the vein, to forming a seal with each other, without experiencing interference with the other free edges. This property allows the device to collapse to form a very low delivery profile, preferably less than 0.25 cm.

Preferably, the prosthetic venous valve provides a sinus, or slightly increased diameter, immediately behind the upstream side of the cusps. Similar to the function of the Sinuses of Valsalva, this sinus assists the valve in closing when pressure/flow reverses as it provides a place for blood flow to act on the upstream sides of the cusps.

To further enhance the hydrodynamics of the prosthetic valve, a nozzle configuration may be provided which promotes laminar flow. The nozzle-like cross-sectional variances are preferably present at both the inlet and outlet ends of the prosthesis. In addition to facilitating laminar blood flow, the resultant increase in velocity past the cusps lessens the likelihood of thrombosis/thrombus formation behind the valve, which may eventually occlude the valve. As mentioned above, the porous material promotes an initial thrombus formation on the cusp material, however, once formed, the smooth, natural surface of the biologic growth, combined with the nozzle effect, will act to prevent excessive thrombus development.

Like the venuloplasty ring, the prosthetic valve preferably includes a grabbing mechanism. The mechanism comprises projections or adhesives which grab the inner walls of the vein. An inflatable or mechanical expansion device is used to expand the diameter of the prosthetic until positive contact is established between the grabbing mechanism and the vein, and then the expansion device is removed. The prosthetic valve returns to its desired size, pulling the vein inward to assume a similar diameter and to form a seal between the vein and the valve. Additionally, the ends of the support structure might be spiral in nature, for anchoring the device into the vein. The spiral arrangement may comprise a fibrous or metallic structure.

The design of the prosthetic valve lends itself to the adaptation of uni-, bi-, and tricuspid embodiments. This allows a selection to be made which closely imitates the native valve being replaced. The cusps, again, are a porous membrane, optimized for cellular ingrowth, yet remain very thin and flexible to permit movement. Combining the flexibility in size selection, the number of cusps, and that cell ingrowth will result in an endothelial lining that eventually provides a totally cellular surface for presentation to the blood contacting surfaces, the resulting valve may become essentially identical to the replaced native valve.

The venuloplasty rings and prosthetic valves of the present invention must exhibit resilient properties. Veins are located closer to the epidermis than arteries, and thus undergo frequent compression as a person comes into contact with various objects. Therefore, the rings and valves must be capable of returning to their desired circular or elliptical shape so that they may resume their intended function. Also, the device is preferably constrained in its ability to expand. Specifically, each device is made with a predetermined maximum diameter such that the device cannot become dilated to the extent that the repaired or replaced valve becomes incompetent through the progressive enlargement of the vein.

Additionally, in order to aid in the initial placement and subsequent identification of these devices, a preferred embodiment includes radiopaque fiber(s) in the structural material. These fibers allow the visualization of the device by fluoroscopy or X-ray. Inclusion of these fibers in the cusps of the prosthetic valve would allow monitoring the movement of the cusps using fluoroscopy.

Though the various embodiments of the aforementioned devices using porous materials involved promoting biologic ingrowth via thrombosis, the device membranes may also accomplish the spirit of the invention without the presence of thrombus. Cells may arrive at the site directly without a thrombus intermediate.

The biologic nature of the structure dictates that it can regenerate critical molecules and biologic function using the cells already present to synthesize such molecules. For example, collagen synthesis may occur that continues to make the structure strong even as older collagen disappears. The structure may thus become self-sustaining.

Additionally, the cells of the device may be grown into the structure from outside sources. For example, cell culture techniques might be utilized to seed the device in vitro with autologous or non-related cells prior to implant. As the device is implanted, it then becomes a biologic structure immediately. Such cells may also be recombinant, or transfected with one or more genes to produce substances beneficial to the device function. Such cells may also be self-propagating to promote longevity of the device and function.

DETAILED DESCRIPTION OF THE INVENTION

Figure 1:
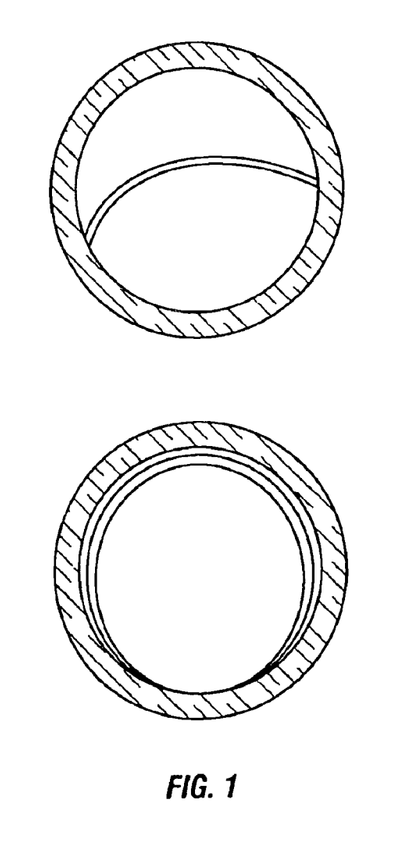
FIG. 1 is an axial cross section of a unicuspid venous valve rendered incompetent due to dilation, and an axial cross section of a healthy unicuspid venous valve below it for comparison.
Figure 2:
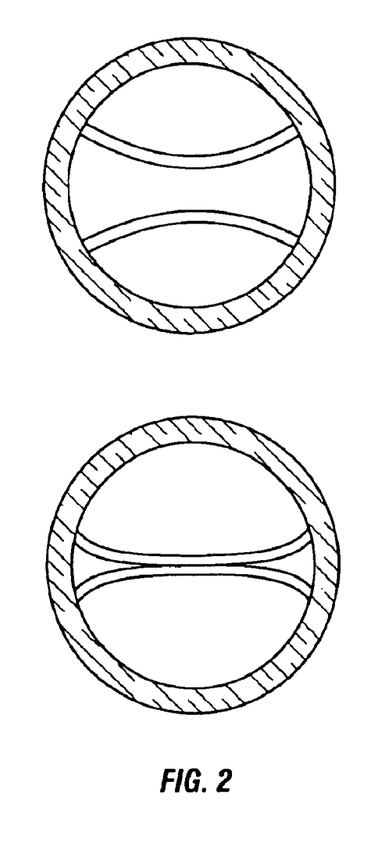
FIG. 2 is an axial cross section of a bicuspid venous valve rendered incompetent due to dilation, and an axial cross section of a healthy bicuspid venous valve below it for comparison.
Figure 3:
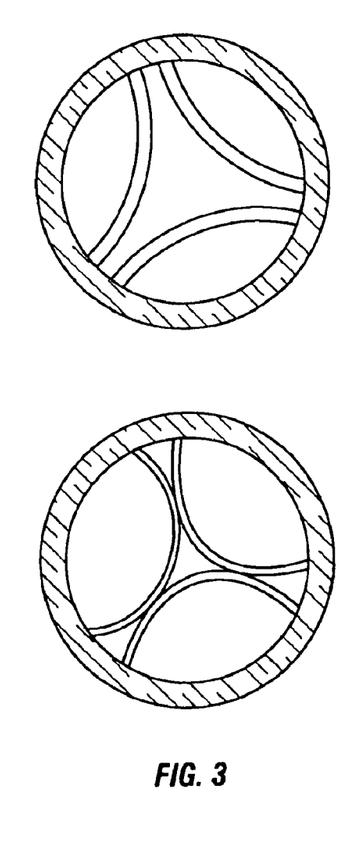
FIG. 3 is an axial cross section of a tricuspid venous valve rendered incompetent due to dilation, and an axial cross section of a healthy tricuspid venous valve below it for comparison.

Referring now to the figures, and first to FIGS. 1 through 3, there are shown examples of unicuspid, bicuspid and tricuspid valves which have become so dilated that they have been rendered incompetent. Below each of the dilated valves, a healthy valve is shown for comparative reference.

Figure 4:
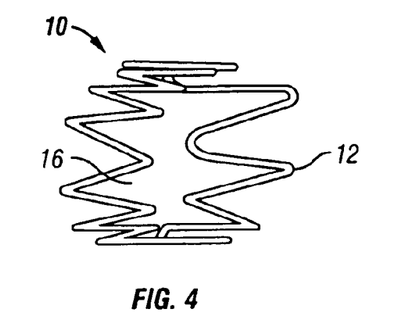
FIG. 4 is a perspective view of a preferred device of the present invention.
Figure 5:
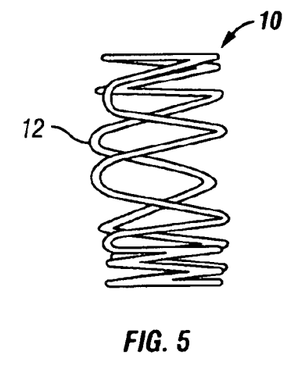
FIG. 5 is a side elevation of the device of FIG. 4.
Figure 6:
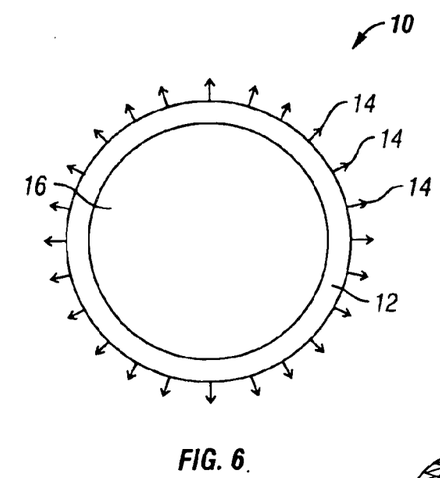
FIG. 6 is a top plan view of the device of FIG. 4.

FIGS. 4–6 show a device 10 of the present invention, useable to reduce the diameter of a dilated vein such that competence may be restored. Device 10 generally comprises a support structure 12 and a grabbing mechanism 14 (shown only on FIG. 6 for clarity).

Figure 7:
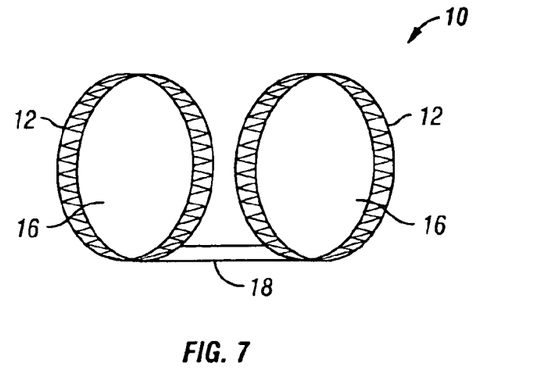
FIG. 7 is a perspective view of a preferred ring assembly of the present invention.

Support structure 12 is shown as a zig-zag patterned spring member curled to form a ring. The zig-zag patterned spring member allows energy to be stored in the bends of the spring when manipulated, and used to return the structure 12 to its original, ring-like configuration when released. One skilled in the art will realize that other structures also acceptably provide such a resilient characteristic. Examples include, but are not limited to, woven strands, coil springs, and the like. The support structure 12 defines an inner passage 16, useable to allow blood to pass therethrough when the device 10 is used within the lumen of a vein, or to allow the vein to pass therethrough when the device 10 is used around the outside of the vein. FIG. 7 shows an alternate embodiment of device 10 whereby two support structures 12 are coupled with a cross member 18 to form a ring assembly. The combination of the two support structures 12 and the cross member 18 provides additional support especially useful in positioning the device 10 within the vein. Cross member 18 helps ensure that the support structures 12 are generally perpendicular to the longitudinal axis of the vein. It is envisioned that the cross member 18 is made of a bioabsorbable material as, once the support structures 12 are attached to the vein walls with the grabbing mechanism 14, the support provided by the cross member 18 is no longer necessary.

Figure 8:
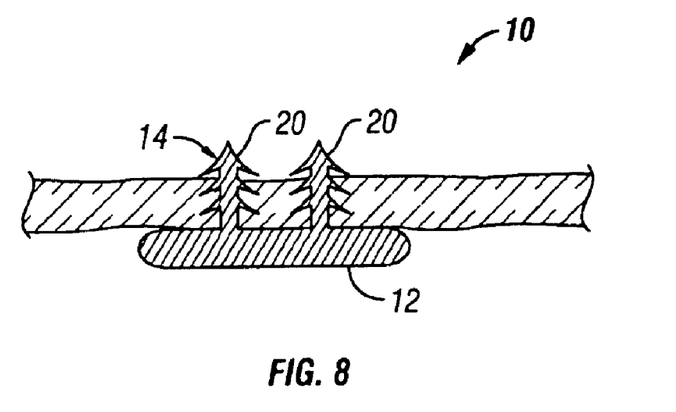
FIG. 8 is a sectional elevation of a grabbing mechanism of the present invention operably attached to vein tissue.
Figure 9:
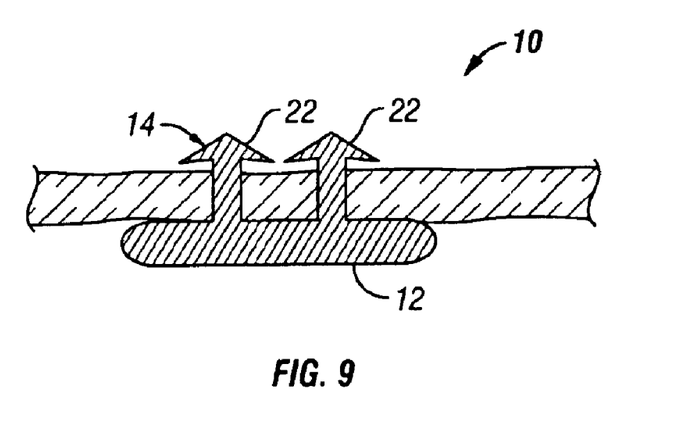
FIG. 9 is a sectional elevation of an alternate grabbing mechanism of the present invention, operably attached to vein tissue.
Figure 10:
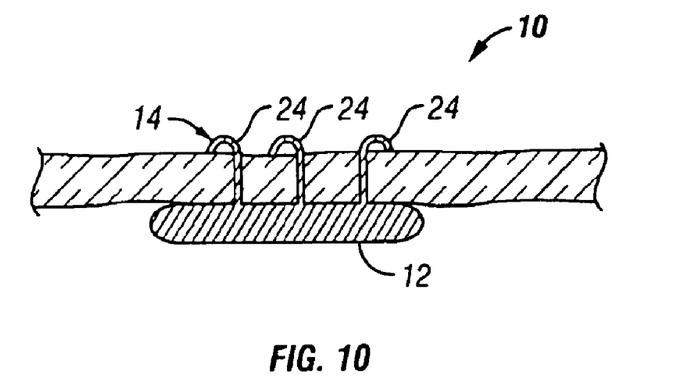
FIG. 10 is a sectional elevation of an alternate grabbing mechanism of the present invention, operably attached to vein tissue.

The grabbing mechanism 14 is a mechanism for adhering the device 10 to the interior or exterior walls of the vein. The grabbing mechanism 14 is especially necessary when the device 10 is implanted within the vein as the vein walls must be pulled inwardly. The grabbing mechanism 14 preferably includes a plurality of projections capable of penetrating and catching the walls of the vein. Referring to FIGS. 8–10, there are shown various embodiments of the grabbing mechanism 14 having projections capable of penetrating and catching the walls of the vein. FIG. 8 shows barbed projections 20, FIG. 9 shows umbrella projections 22 which expand after having passed completely through the vein wall, and FIG. 10 shows hook projections. Alternatively or additionally, an adhesive (not shown) could be used for bonding the support structure to the vein wall.

Figure 11:
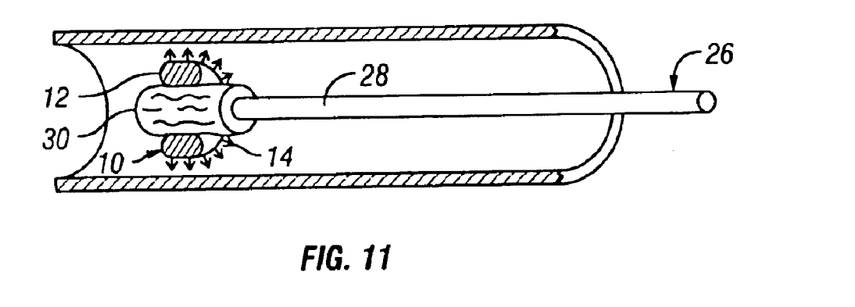
FIG. 11 is a sectional view of a device being placed percutaneously in a vein using an expansion system of the present invention and a catheter delivery system for placement.
Figure 12:
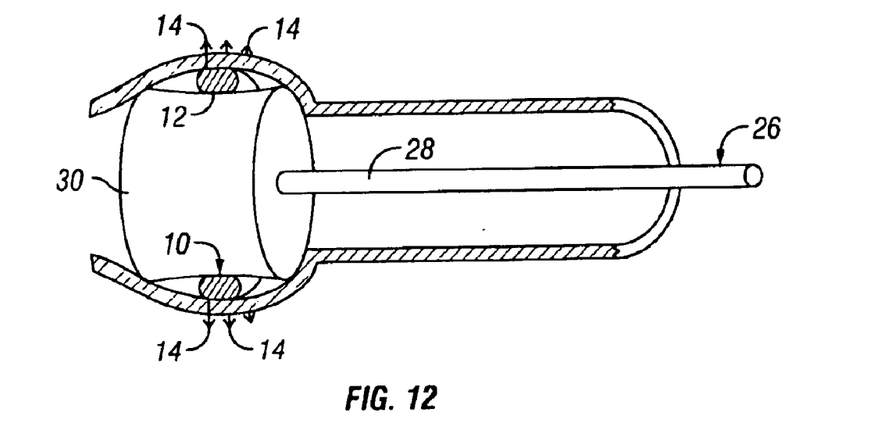
FIG. 12 is a sectional view of the device being expanded by the expansion system of FIG. 11.
Figure 13:
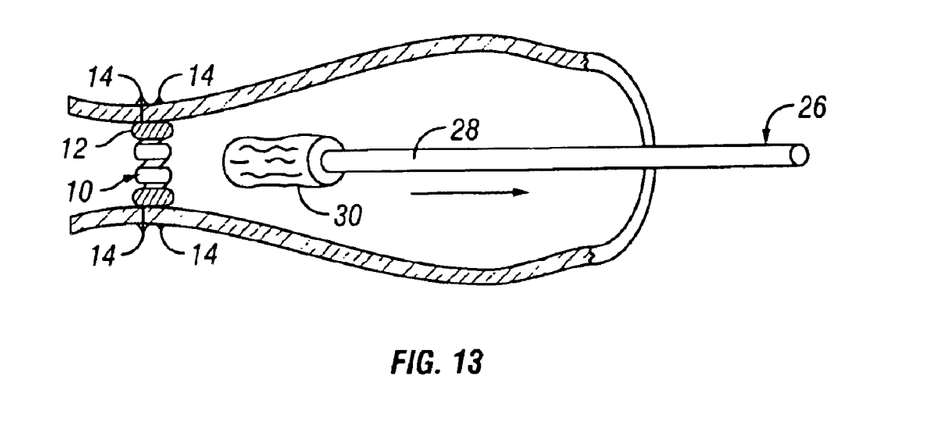
FIG. 13 is a sectional view of the device being left in the vein while the expansion system of FIG. 11 is being removed from the vein.

Each of the grabbing mechanisms 14 require some sort of initial contact force between the vein wall and the device 10. In the case of percutaneously placing the device within the lumen of the vein, contact between the vein and the grabbing mechanism 14 is established using an expansion system 26. As best seen in FIGS. 11–13 the expansion system 26 is used to increase the diameter of the support structure 12 until the outer diameter of the device 10 exceeds the inner diameter of the vein, thereby forcing the projections of the grabbing mechanism 14 through the vein wall. The expansion system 26 is then retracted and removed, allowing the spring characteristics of the support structure 12 to restore the device 10 to approximately the original diameter, thereby contracting the vein to a desired size as the grabbing mechanism 14 maintains positive contact between the device 10 and the vein. FIGS. 11–13 show an inflatable expansion system 26 generally comprising a delivery tube 28 and an inflatable bladder 30, operably attached to the distal end of the delivery tube 28 such that an inner lumen of the delivery tube 28 is in fluid communication with an interior of the bladder 30. In FIG. 11, the expansion system 26 is introduced into the inner lumen of the vein, with the bladder 30 deflated, and a device 10 operably disposed around the outside of the deflated bladder 30. The projections of the grabbing mechanism 14 are disposed around the outside circumference of the support structure 12.

In FIG. 12, the device 10 has reached the target site and the bladder 30 is inflated through the delivery tube 28. Inflation continues until the projections of the grabbing mechanism 14 protrude through the vein wall.

In FIG. 13, the bladder 30 is deflated, again through the inner lumen of the delivery tube 28, and retracted. The spring action of the support structure 12, combined with the vein gripping power of the grabbing mechanism 14, constrict the vein to a smaller diameter. Preferably, this method is performed in close proximity to one or both sides of an incompetent venous valve, thereby bringing the free edges of the cusps in close enough proximity to each other to regain competence.

Figure 14:
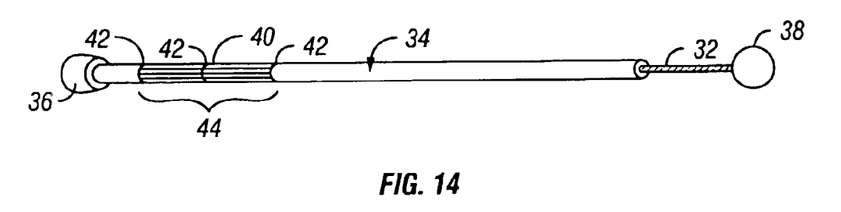
FIG. 14 is a perspective view of an alternative expansion system of the present invention.
Figure 15:
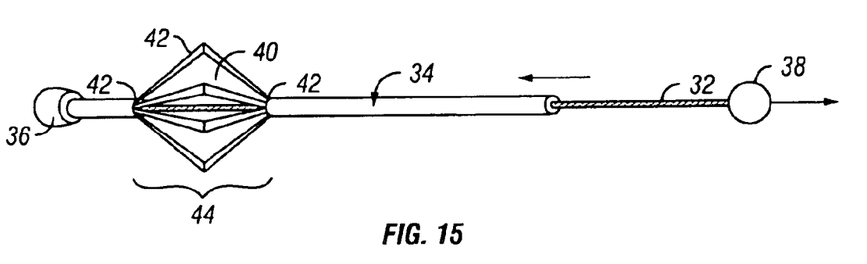
FIG. 15 is a perspective view of the expansion system of FIG. 14 being expanded.

FIGS. 14 and 15 show a non-inflatable, mechanical embodiment of the expansion system 26. A pull wire 32 is operably disposed through the inner lumen of a tube-like body 34. The pull wire 32 includes a catch-ball 36 at its distal end and a finger grip 38 at its proximal end. The body 34 includes an expansion section 44 defined by a plurality of longitudinal slots 40 and circumferential scores 42. The slots 40 extend all the way through to the inner lumen. The scores 42 do not extend to the inner lumen, rather, they provide bending points for the expansion section 44. FIG. 15 shows that when the finger grip 38 is used to pull the pull wire 32 proximally, relative to the body 34, the catch ball 36 shortens the body 34, causing the expansion section 44 to bend outwardly. The catch ball 36, the expansion section 44, or, more preferably, the support structure 12 of the device 10 may include radiopaque fibers to assist in viewing the percutaneous delivery of the device 10 to the target site.

Figure 16:
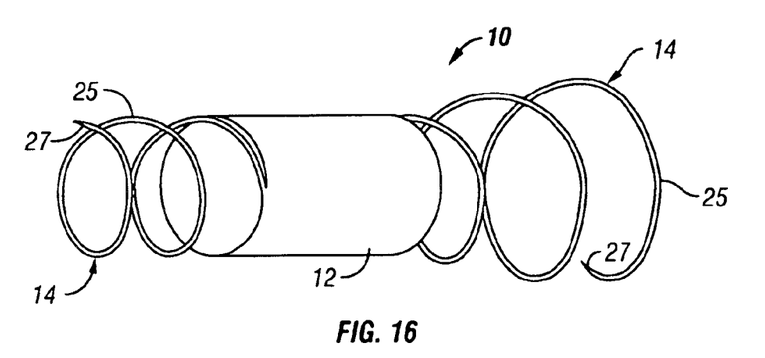
FIG. 16 is a perspective view of an alternative grabbing mechanism of the present invention.

FIG. 16 shows an alternative embodiment of a grabbing mechanism 14 of the present invention, which requires no expansion system 26. From one or both sides of the support structure 12, extends spiral members 25 having slightly sharpened ends 27. The spiral members 25 are shown radiating longitudinally and radially, and are constructed and arranged to be biased as such, thereby obviating the need for an expansion system 26 to establish positive contact between the ends 27 and the vein walls. It may be desired to provide spiral members 25 which are constructed and arranged to radiate primarily radially, thereby reducing the overall length of the device 10.

Figure 17:
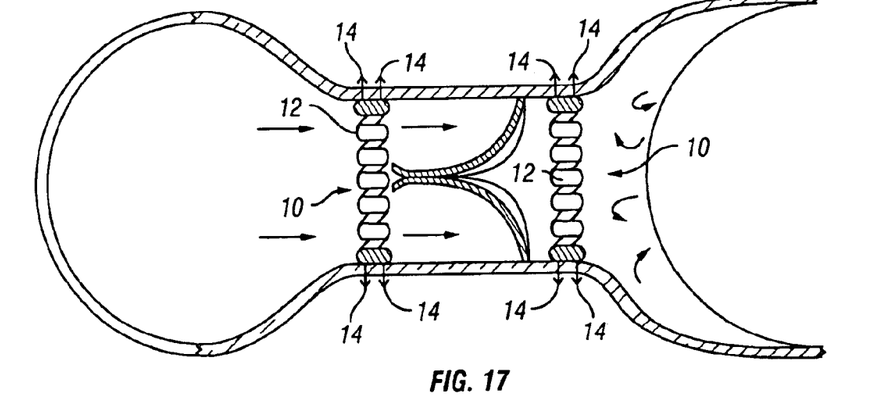
FIG. 17 is a is a longitudinal cutaway view of a dilated bicuspid valve rendered competent by the device of the present invention, the valve shown preventing blood from flowing in a reverse direction.
Figure 18:
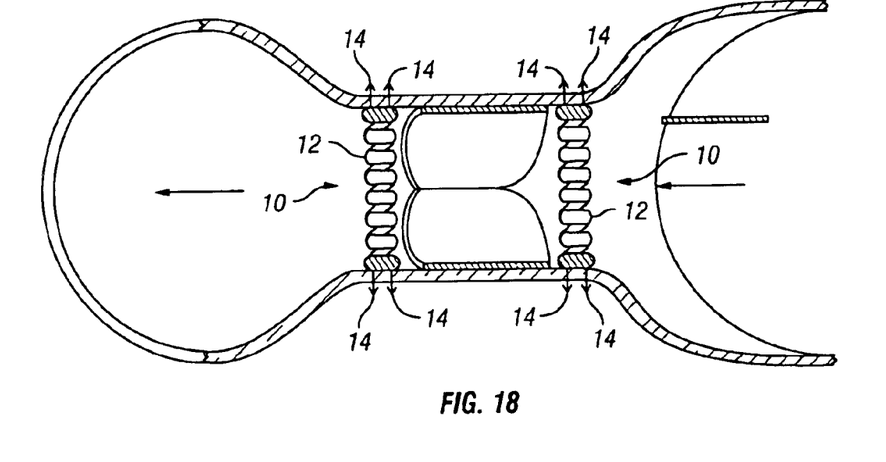
FIG. 18 is a longitudinal cutaway view of the dilated bicuspid valve of FIG. 17, the valve shown allowing blood to flow in a forward direction.

FIGS. 17–20 show the device 10 in place and restoring competence to a venous valve. In FIG. 17, a device 10 has been implanted on either side of a native bicuspid valve. The vein is shown cutaway longitudinally such that the two cusps of the valve are sectioned along the middle. In FIG. 17, the blood is attempting to flow in a reverse direction as indicated by the arrows. The inflated cusps have coapted, thereby blocking the flow of blood in the reverse direction, as indicated by the curly arrows depicting eddies in the blood flow. In FIG. 18, the blood is flowing in a direction toward the heart, thereby causing the cusps to lie flat against the inner walls of the vein. The blood flows freely past the cusps and through the inner passages 16 of the devices 10. Note that the grabbing mechanism 14 is fully protruding through the vein walls, holding the support structure 12 in place.

Figure 19:
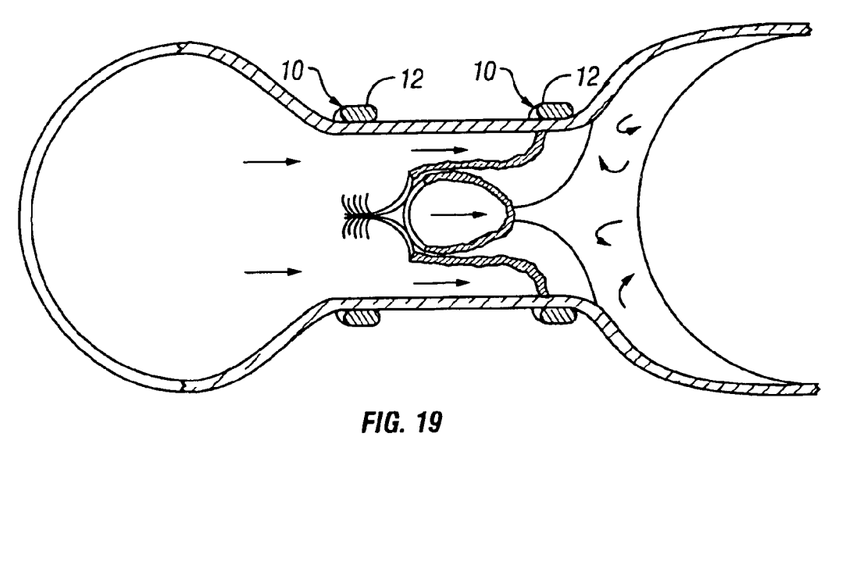
FIG. 19 is a is a longitudinal cutaway view of a dilated tricuspid valve rendered competent by the device of the present invention, the valve shown preventing blood from flowing in a reverse direction.
Figure 20:
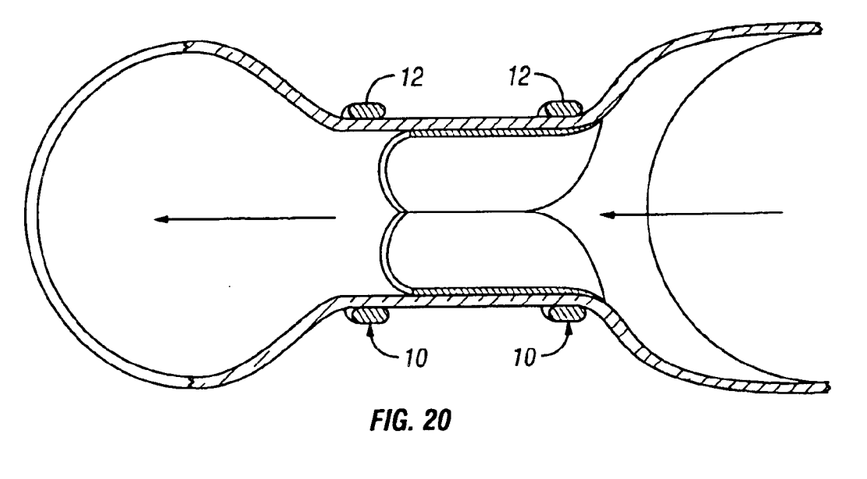
FIG. 20 is a longitudinal cutaway view of the dilated tricuspid valve of FIG. 19, the valve shown allowing blood to flow in a forward direction.

FIGS. 19 and 20 show a device 10 installed on the outside of a vein, yet having the same effect of restoring competency to, this time, a tricuspid valve. Again, FIG. 19 shows the blood attempting to flow in a reverse direction as indicated by the arrows. The three inflated cusps have coapted, thereby blocking the flow of blood in the reverse direction, as indicated by the curly arrows depicting eddies in the blood flow. The vein is once again shown cutaway longitudinally, sectioning the three cusps. Only a small segment of the third cusp is shown as it attaches on either side to that section of the vein which is cutaway.

Notably, no grabbing mechanism 14 is shown in FIGS. 19 and 20. When the device 10 is installed on the outside of the vein, it may be unnecessary to use grabbing mechanisms 14. However, if necessary, an adhesive around the inner circumference of the support structure 12 may be used. Else, it may be preferred to use a projection type grabbing mechanism 14, such as inwardly projecting barbed projections 20, extending from the inner side of the support structure 12.

Figures 21, 22:
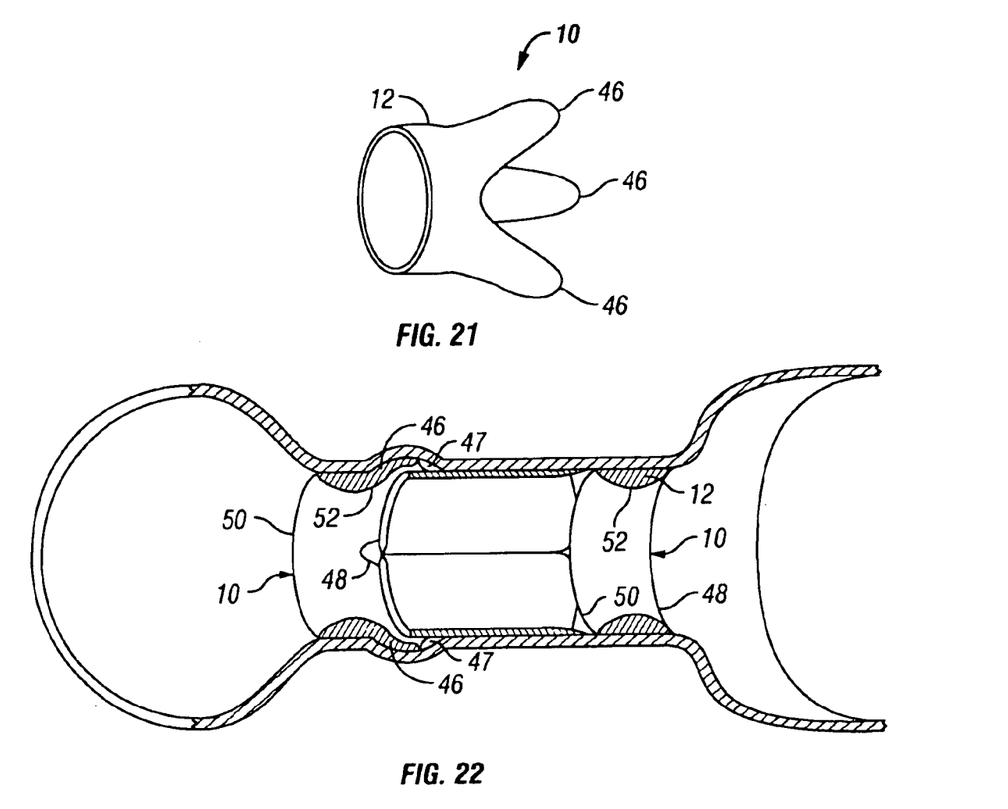
FIG. 21 is a perspective view of a device of the present invention having fingers for creating sinuses.
FIG. 22 is a longitudinal cutaway view of a dilated bicuspid valve rendered competent by two devices of the present invention having hydrodynamic cross sections creating a nozzle effect

Occasionally, a valve may fail when a cusp lies flat against the vein wall such that the cusp presents insufficient sail area to the blood flow to catch blood between the cusp and the wall. The blood thus just flows past the cusp, which never inflates. The aortic valve, being an extremely vital arterial valve, has been naturally equipped with a solution behind each cusp—the Sinuses of Valsalva. The Sinuses of Valsalva refer to a natural cavity behind each of the three cusps, which prevent the cusps from being able to seal themselves to the wall. Depicted in FIGS. 21 and 22, and inspired by the Sinuses of Valvsalva, one embodiment of the device 10 provides an artificial remedy to this type of valve failure. Referring first to FIG. 21, there is shown a device 10 having a support structure 12 and three longitudinal fingers 46 extending from an upstream side of the support structure 12 and angling radially outwardly. The fingers 46 are insertable behind the cusps of a native valve. FIG. 21 depicts a three-fingered embodiment for a tricuspid valve but it is understood that two- and one-fingered embodiments would be used for bi- and unicuspid valves, respectfully. The outward angle of the fingers 46 slightly stretch the vein wall away from the outer side of the cusp, thereby forming a sinus 47 therebetween. FIG. 21 shows a device 10 having fingers 46 in place behind a native tricuspid valve.

Also shown in FIG. 21 are two devices 10 having hydrodynamic cross sections. The cross sections of the support structures 12 are constructed and arranged to form a nozzle configuration which promotes laminar flow. Specifically, the support structures 12 define an inlet edge 48 and an outlet edge 50 with a contoured section 52 therebetween. The contoured area creates, in the blood flow, an increase in pressure which is released and converted to increased velocity beyond the device 10. When such contoured devices 10 are placed on either side of the native valve, in addition to facilitating laminar blood flow, the resultant increase in velocity past the cusps lessens the likelihood of thrombosis/thrombus formation behind the valve, which may eventually occlude the valve.

Figure 23:
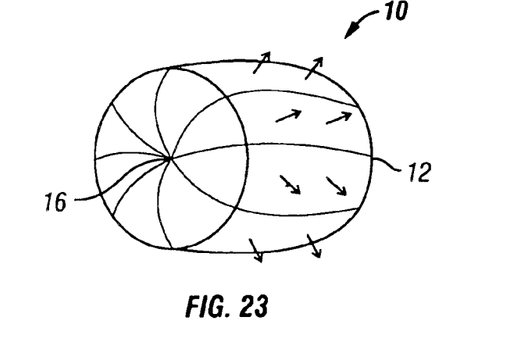
FIG. 23 is a perspective view of a device of the present invention which is constructed and arranged to occlude a valve when released.
Figure 24:
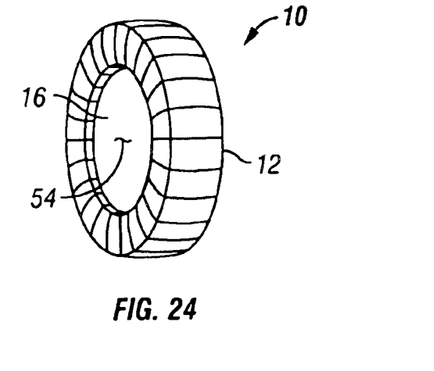
FIG. 24 is a perspective view of an alternative occluding device of the present invention.

Conversely, there may be some instances when it is desired to occlude a venous valve or vein, either temporarily or permanently. FIGS. 23 and 24 show two embodiments of a device 10 which, when released, prevents blood from flowing through or around the device 10 in either direction. FIG. 23 shows a device 10 whereby the support structure 12 is constructed and arranged to reduce the inner passage 16 to such a small diameter, as to allow negligible blood flow therethrough. FIG. 24 shows an alternate approach by providing a device 10 having a support structure 12 defining the inner passage 16 but also including a membrane 54 which is extends across the inner passage 16 preventing blood from flowing therethrough.

Figure 25:
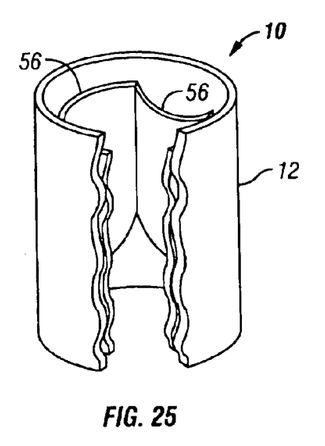
FIG. 25 is a perspective view of a device of the present invention having two prosthetic cusps to form a prosthetic bicuspid valve, with a part of the device cutaway to show detail.
Figure 26:
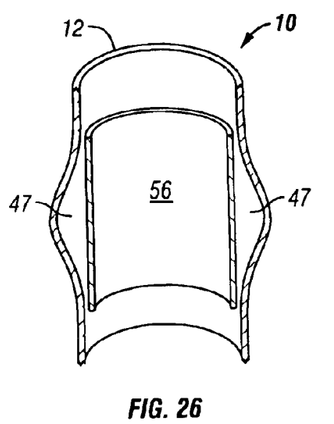
FIG. 26 is a sectional perspective view of a device of the present invention having one prosthetic cusp to form a unicuspid valve and further having a support structure constructed and arranged to form a sinus behind the cusp; and, FIG. 27 is a sectional perspective view of a device of the present invention having three prosthetic cusps, two of which are shown, to form a tricuspid valve and further having a support structure constructed and arranged to a nozzle effect.
Figure 27:
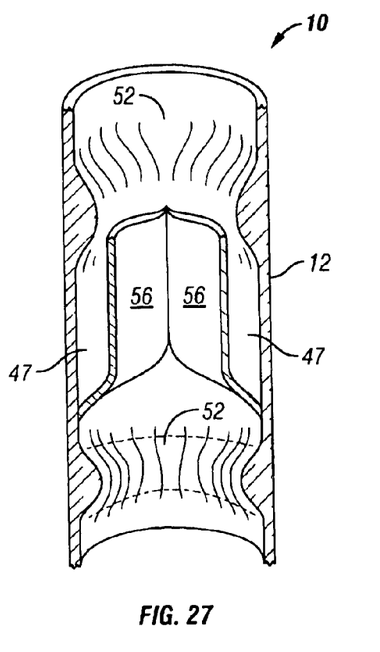

Referring now to FIGS. 25–27, there are shown three embodiments of the device 10 further comprising prosthetic cusps 56. These prosthetic cusps 56 are intended to be used to replace native cusps when the latter are damaged or otherwise rendered incompetent and cannot regain competency through constriction. The prosthetic cusps 56, though shown as being relatively thick in the Figures for clarity, are extremely thin. Preferably, the cusps 56 are less than 100 micrometers thick. Whether unicuspid, bicuspid, or tricuspid, the cusps 56 are constructed and arranged within the support structure 12 to mimic native valves.

FIG. 25 shows a device 10 having two prosthetic cusps 56 to form a bicuspid valve. For detail purposes, one cusp 56 is shown inflated while the other is shown deflated.

FIG. 26 shows a device 10 having one prosthetic cusp 56 to form a unicuspid valve. The device 10 has a support structure which is shaped to bow outwardly around the cusp 56 in order to create a sinus 47 between the cusp 56 and the inner wall of the support structure. More than 3 cusps is also a design that is envisioned.

FIG. 27 shows a device 10 creating a tricuspid valve, though only two cusps 56 are shown as the third is cut away. The device 10 has a support structure 10 which includes the aforementioned contoured areas 52 upstream and downstream of the cusps 56 to create a nozzle effect. Note how the contoured areas 52 also form sinuses 47 behind the cusps 56.

The prosthetic venous valve cusps 56 of the present invention are preferably porous, permitting them to become living structures as cellular ingrowth is facilitated by the fibers. At the same time, the material performs biologic functions, such as providing an anti-coagulant, if and when an endothelial lining develops. The porosity of the device 10 permits fibrin and/or platelet thrombus to form within the matrix. The "healing" process will thus result in tissue growth including endothelialization. The pore size is preferably between 10 and 100 microns. Additionally, the pores are of an interconnected, "open pore" structure. Thus, the pores are constructed and arranged to encourage cell ingrowth and vascularization/angiogenesis, thereby further supporting the structure.

In addition to the cusps 56, the support structure 12 may be partially made from the same fiber arrangement, permitting the support structure to also become a living structure once the pores fill with thrombus and "heal" with cells. The support structure may be coated with a biomolecule and/or heparin to assist in cell ingrowth and anti-thrombogenicity.

Once infiltrated, the device surfaces become completely biologic, preventing blood flow from contacting anything other than the newly developed, natural cells. The device may further be bioabsorbable, becoming resorbed by the body after a predetermined period, thereby leaving a cuff of biologic tissue that performs the diameter reduction function by way of the newly grown fibrous tissue.

The material of the device 10 may be coated to enhance cellular ingrowth. This coating may comprise fibrin, fibronectin, elastin, elastin fragments, collagen, mucopolysaccharides, glycosaminoglycans, extracellular matrix, taxol, or other biomolecule useful for attracting and keeping cells and fibroblasts and/or myofibroblasts at the site. The coating may further include a drug eluting substance, such as rapamycin, actinomycin D, taxol/taxanes or other agents, to prevent cell overgrowth or extraacellular matrix production.

Further, the material and dimensions are such that the device may be collapsible to the extent that the ring responds to natural muscle contractions. Thus, the device 10 should not interfere with the circulatory system's natural physiologic pumping action.

Though not shown in the Figures, another aspect of the present invention includes an imbedded transducer. Recent advances in transducer miniaturization make it possible to attach one or more transducers to the disclosed device 10. These transducers may be used to measure blood pressure, flow, temperature, thrombosis, or other physiologic variables.

Though the various embodiments of the aforementioned devices 10 using porous materials involved promoting biologic ingrowth via thrombosis, the device membranes may also accomplish the spirit of the invention without the presence of thrombus. Cells may arrive at the site directly without a thrombus intermediate.

The biologic nature of the structure dictates that it can regenerate critical molecules and biologic function using the cells already present to synthesize such molecules. For example, collagen synthesis may occur that continues to make the structure strong even as older collagen disappears. The structure may thus become self-sustaining.

Additionally, the cells of the device may be grown into the structure 12 from outside sources. For example, cell culture techniques might be utilized to seed the device 10 in vitro with autologous or non-related cells prior to implant. As the device 10 is implanted, it then becomes a biologic structure immediately. Such cells may also be recombinant, or transfected with one or more genes to produce substances beneficial to the device function. Such cells may also be self-propagating to promote longevity of the device and function.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of restoring competence to a dilated venous valve comprising:
    providing a constricting device, attachable to the vein, and capable of circumferentially compressing the vein;
    providing a grabbing mechanism on a surface of the constricting device for contacting said vein;
    placing the constricting device proximate the venous valve;
    attaching the constriction device to the vein;
    using the constricting device to compress the vein to a predetermined diameter whereby cusps of the venous valve coapt, thereby restoring competence to the venous valve; and
    wherein placing the constricting device proximate the venous valve comprises placing the constricting device around the outside of the vein.

2. The method of claim 1 wherein placing the constricting device around the outside of the vein further includes stretching the constricting device, thereby increasing an inner diameter of the constricting constricting device, thereby increasing an inner diameter of the constricting device such that the constricting device has a larger inside diameter than an outside diameter of the vein proximate to venous valve.

3. The method of claim 2 wherein attaching the constricting device to the vein comprises releasing the constricting device, thereby allowing the constricting device to return to an initial, predetermined diameter that is smaller than the outside diameter of the vein proximate the venous valve.

4. A method of restoring competence to a dilated venous valve comprising:
    providing a constricting device attachable to the vein, and capable of circumferentially compressing the vein;
    providing a grabbing mechanism around an outside circumference of the constricting device;
    percutaneously placing the constricting device proximate the venous valve;
    placing an expansion device within an open center defined by the constricting device;
    expanding the constriction device using the expansion device until the outside circumference of the constriction device is larger in diameter than an inner diameter of the vein, thereby forcing contact between the circumference of the constricting device and the vein; and
    using the constricting device to compress the vein to a predetermined diameter whereby cusps of the venous valve coapt, thereby restoring competence to the venous valve.

5. The method of claim 4 wherein using the constricting device to compress the vein comprises releasing the expansion device, thereby allowing the constricting device to return to a predetermined diameter smaller than the inner diameter of the vein, thereby pulling the vein inwardly and compressing the vein to the predetermined diameter.

6. The method of claim 4, wherein providing a grabbing mechanism includes providing umbrella projections which expand after having passed through an inner wall of said vein.

7. The method of claim 4, wherein expanding the constriction device includes urging the grabbing mechanism through said inner wall of said vein.

8. The method of claim 7, wherein urging the grabbing mechanism through the vein wall includes causing the grabbing mechanism to protrude through said inner wall of said vein.

9. The method of claim 4, further comprising providing a second constricting device and using said second constricting device to also compress the vein to a predetermined diameter whereby cusps of the venous valve coapt, thereby restoring competence to the venous valve.

10. The method of claim 4, wherein expanding the expansion device includes inflating the expansion device.

11. The method of claim 4, wherein expanding the expansion device includes mechanically expanding the expansion device.

12. The method of claim 4, further comprising providing a leaflet support structure on said constricting device.

13. The method of claim 4, wherein providing a constricting device includes providing a support structure having a zig zag patterned spring member curled to form a ring.

14. A method of restoring competence to a dilated venous valve comprising:
 providing a first constricting device, attachable to the vein, and capable of circumferentially compressing the vein;
 placing the first constricting device proximate the venous valve;
 attaching the constricting device proximate the venous valve; and
 using the first constricting device to compress the vein to a predetermined diameter;
 providing a second constricting device, attachable to the vein, and capable of circumferentially compressing the vein;
 placing the second constricting device proximate the venous valve, opposite the first constricting device, such that the venous valve is juxtaposed between the two constricting devices;
 attaching the second constricting device to the vein;
 using the second constricting device to further compress the vein to the predetermined diameter whereby the cusps of the venous valve coapt, thereby restoring competence to the venous valve.

15. The method of claim 14, wherein the attaching of said first constricting device and the attaching of said second constricting device comprises attaching said first and second constricting devices to the internal wall of said vein.

16. The method of claim 14, wherein the attaching of said first constricting device and the attaching of said second constricting device comprises attaching said first and second constricting devices to an external wall of said vein.

17. The method of claim 14, wherein the providing of said first and second constricting devices includes the first and second constricting devices being attached to each other.

18. The method of claim 14, wherein the attaching of said first and second constricting device includes expanding said first and second constricting devices against an internal wall of said vein.

19. The method of claim 14, further comprising providing a grabbing mechanism on each said first and second constricting devices.

20. The method of claim 19, wherein the attaching of said first and second constricting devices includes urging said grabbing mechanism of both said first and second constricting devices through an internal wall of said vein.

* * * * *